United States Patent [19]

Mahajan et al.

[11] Patent Number: 4,992,480

[45] Date of Patent: Feb. 12, 1991

[54] HOMOGENEOUS CATALYST FORMULATIONS FOR METHANOL PRODUCTION

[75] Inventors: Devinder Mahajan, Port Jefferson; Richard S. Sapienza, Shoreham; William A. Slegeir, Hampton Bays; Thomas E. O'Hare, Huntington Station, all of N.Y.

[73] Assignee: Associated Universities, Inc., Washington, D.C.

[21] Appl. No.: 500,935

[22] Filed: Mar. 29, 1990

Related U.S. Application Data

[60] Division of Ser. No. 141,454, Jan. 7, 1988, Pat. No. 4,935,395, which is a continuation-in-part of Ser. No. 943,731, Dec. 19, 1986, abandoned.

[51] Int. Cl.$^5$ .............................................. C07C 27/06
[52] U.S. Cl. .................................................... 518/700
[58] Field of Search ......................................... 518/700

[56] References Cited

U.S. PATENT DOCUMENTS 4,623,634  11/1986  Sapienza et al. ..................... 518/700
4,731,386  3/1988   Onsagen .............................. 518/700

*Primary Examiner*—Howard T. Mars
*Attorney, Agent, or Firm*—Margaret C. Bogosian

[57] ABSTRACT

There is disclosed synthesis of $CH_3OH$ from carbon monoxide and hydrogen using an extremely active homogeneous catalyst for methanol synthesis directly from synthesis gas. The catalyst operates preferably between 100°–150° C. and preferably at 100–150 psia synthesis gas to produce methanol. Use can be made of syngas mixtures which contain considerable quantities of other gases, such as nitrogen, methane or excess hydrogen. The catalyst is composed of two components: (a) a transition metal carbonyl complex and (b) an alkoxide component. In the simplest formulation, component (a) is a complex of nickel tetracarbonyl and component (b) is methoxide ($CH_3O^-$), both being dissolved in a methanol solvent system. The presence of a co-solvent such as p-dioxane, THF, polyalcohols, ethers, hydrocarbons, and crown ethers accelerates the methanol synthesis reaction.

11 Claims, No Drawings

HOMOGENEOUS CATALYST FORMULATIONS FOR METHANOL PRODUCTION

The U.S. Government has right in this invention pursuant to Contract No. DE-AC02-76H00016, between the U.S. Department of Energy and Associated Universities Inc.

RELATED APPLICATIONS

This application is a divisional of application Ser. No. 141,454 filed Jan. 7, 1988, now U.S. patent Ser. No. 4935395 which is a continuation-in-part of application Ser. No. 943,731, filed Dec. 19, 1986 and now abandoned.

BACKGROUND OF THE INVENTION

This invention relates to novel homogeneous catalyst formulations for methanol production. These new formulations have a number of features: liquid phase performance, low temperature, low pressure performance, high activity, and high selectivity, which permits gas conversions in one pass through greater than 90%, and under optimum conditions gas conversions of about 97%. Since this catalyst system is a liquid phase system, it permits the reaction between carbon monoxide and hydrogen to form methanol, which is an exothermic reaction, to proceed at fully isothermal conditions. In contrast, the traditional pelleted, solid catalysts used in methanol production create hot spots in the reactor which prevent the process from operating efficiently. Further, because the homogeneous catalyst is in solution, reaction heat removal can be decoupled from kinetics. Thus, unlike existing processes, with the instant process optimum performance, both chemically and thermally, can be built into the production system separately, with the components of the production system designed to optimize heat removal and kinetics.

The homogeneous catalyst formulation of the present invention overcome other disadvantages of conventional, solid-phase, methanol synthesis catalysts. Typically, conventional processes require high temperatures (250° C.) and high pressure (765 psi) and are limited by the low equilibrium conversion (60%). Using the catalysts of the present invention, methanol production can be conducted at low temperatures and pressure with a high equilibrium conversion.

Further, conventional type catalysts, such as pellet type catalysts, usually exhibit a gas conversion rate of about 16–30% per pass, necessitating the re-cycling of the feed gas in order to operate the production system at an economically acceptable efficiency. Thus, although partial oxidation of natural gas yields an ideal methanol feed gas, partial oxidation cannot be used to produce the feed gas for conventional catalyst systems because such systems require a feed gas with very low levels of inert gases, especially nitrogen. Inerts such as nitrogen that build up in the recycle stream must be kept low for process efficiency. To produce feed gases with low levels of inerts, the partial oxidation would have to be carried out using oxygen and this approach renders this method of feed gas preparation economically unfeasible. The instant catalyst system makes it possible to take advantage of partial oxidation production of the synthesis feed gas because the high conversion eliminates the need for a recycle stream and thereby permits use of air rather than oxygen, saving the large costs for oxygen generation. A further improvement that results from the high efficiency of the process that permits one pass through operation is that the atmospheric nitrogen that enters the system through the air partial oxidation step leaves the reactor at reaction pressure and can be expanded to provide energy, for example for air compression.

The present invention provides a homogeneous catalyst that permits the production of methanol from a synthesis gas feed gas containing inert gases, at low temperatures and pressures and at high gas conversion rates. This represents a significant improvement in reaction conditions and process efficiency over the conventional methanol catalysts.

DETAILED DESCRIPTION OF THE INVENTION

The instant invention covers a novel homogeneous catalyst which can be used for the synthesis of methanol from carbon monoxide and hydrogen. This homogeneous catalyst is easily prepared; it exhibits superior activity when compared to conventional methanol catalysts, it permits the use of lower temperatures and pressures in the reactor, it permits the use of a feed gas that contains inert gases in addition to the CO and $H_2$, and it produces high gas conversion rates.

This homogeneous catalyst of the present invention is comprised of two components dissolved in methanol or a methanol and co-solvent mixture. The two components are a transition metal carbonyl complex and an alkoxide. The transition metal is selected from the group consisting of copper, nickel, palladium, cobalt, ruthenium, iron, molybdenum and mixtures of these metals. The preferred transition metal is nickel.

This two component catalyst is in a solution of methanol, which is available from the methanol product in the reactor. A co-solvent may also be employed, preferably an organic oxygen containing co-solvent that is miscible with methanol. Suitable co-solvents include saturated hydrocarbons, amine based solvents, ethers, esters, alkyl polyethers and hydroxalkylpolyethers in which the carbon chain is interrupted by one or more oxy groups, and alcohols. The preferred co-solvents are tetrahydrofuran, 2-methyltetrahydrofuran, iso-octane, toluene, p-dioxane, t-amyl alcohol, t-butyl alcohol, polyalcohols, glycol derivatives such a polyethylene glycol and triglyme, the dimethyl ether of resorcinol, dimethyl oxalate, and crown ethers.

Because the homogeneous catalyst of the present invention possesses such high activity, the catalyzed production of methanol from carbon monoxide and hydrogen can be carried out under moderate conditions. The catalyst operates effectively at temperatures in the range of from 20° C. to 150° C., with temperatures in the range of 100°–150° C. being preferred. Likewise the pressure prevailing in the reactor can be as low as 50 psi and as high as 300 psi with the preferred pressure being in the range of 100–150 psi.

The feed gas for the production of methanol using the present catalyst is preferably synthesis gas produced by the air partial oxidation of natural gas. This feed gas may be diluted with inert gases such as nitrogen and methane. The catalyst can tolerate minor quantities of hydrogen sulfide, carbon dioxide and water but it is preferred to use an approximately anhydrous, carbon dioxide-free synthesis gas.

The homogeneous catalyst of the present invention is the product of the reaction between the two materials used to prepare the catalyst, the transition metal material and the alkoxide material. The transition metal material is a material capable of generating the corresponding transistion metal carbonyl is methanol solution. The transition metal material may be the metal carbonyl or a carbonyl precursor. As used herein, the term carbonyl precursor means a material which, when dissolved in methanol, forms the transistion metal carbonyl in situ. The transition metal carbonyl or transition metal carbonyl precursor may be used in the preparation of the instant catalyst in its mononuclear form or in cluster form. With the preferred transition metal, nickel, any form of nickel carbonyl, such as nickel tetracarbonyl, $Ni(CO)_4$, or any carbonyl precursor capable of generating the carbonyl nickelate in the methanol solution can be used in the preparation of the homogeneous catalyst. It is also possible to use a bi-metallic system in which a mixture of two transition metal carbonyls, or carbonyl precursors, is used, for instance nickel carbonyl and molybdenum carbonyl. In another aspect of using a bi-metallic system, a transition metal carbonyl or carbonyl precursor, for instance nickel tetracarbonyl, is used, together with the alkoxide contributing material, such as potassium methoxide, and in addition a transition metal alkoxide is also used, such as copper methoxide.

The transition metal carbonyl or carbonyl precursor material may also be introduced into the methanol solution in which the homogeneous catalyst is to be prepared in the form of any supported species which will form, for instance, the carbonyl nickelate, on its surface. In this way the homogeneous catalyst will be carried on a support, like zeolite, so that the system could function as either a homogeneous or heterogeneous catalyst.

The second material used in the preparation of the homogeneous catalyst is the material that contributes the alkoxide component. Useful as this second reaction material is any metal, amine, or other material which will form or generate alkoxides in the presence of the methanol solvent system. Possible alkoxide generators are group IA, IIA and IIB metal alkoxides, where the alkoxy group is preferably derived from alcohols containing 1-6 carbon atoms. Preferred are the aliphatic alcoholates where the cation is an alkali or alkaline earth metal or a mixture thereof. Most preferred are the aliphatic alcoholates of sodium, potassium, rubidium, cesium, barium and calcium; with potassium methoxide most preferred. Examples of amines that will generate an alkoxide in a methanol solution are 1,8-diazobicyclo[5.4.0]undec-7-ene and tetramethylammonium methoxide.

When the alkoxide contributing material is added to the reactor during preparation of the homogeneous catalyst, it is also possible to add a material that will inactivate the cation or non alkoxide ion through physico-chemical interactions in order to increase the concentration of the alkoxide ion in solution. Suitable complexation and/or coordination materials or ligands for this purpose include crown ethers, crystands and multidentates for alkali and alkaline earth cations. Preferred complexation and/or coordination ligands include 2,2-bipyridines, diethyleneglycoldimethyl ether or 15-Crown-5 with sodium, tetramethylethylenediamine or triethanolamine with lithium, and dibenzo-18-Crown-6 with potassium (see Chem. Rev., 79, 415, 1979).

In a further aspect of the process by which the homogeneous catalyst of the present invention is prepared, it is possible to employ solvent additives that accelerate the reaction of the metal and alkoxide catalyst components. As an example, it is possible to add to the methanol solution nickel carbonyl activators such as sodium sulfide, thioacetamide, mercury ions, borate ions, for instance from boric acid, borate esters, and thioamides such as thiocarboxylic acid amides, thioazole, thioureas, mustard oils, thiocarbamic acid derivatives, thiuram disulfides, and rhodemic acid.

In the preferred homogeneous catalyst formulation, the transitional metal component is a complex of nickel tetracarbonyl and the alkoxide component is the methoxide anion, $MeO^-$, with the preferred associated cation being either an alkali metal (Na, K) or a non-alkali metal such as tetramethylammonium; these preferred cations increase the solubility of the catalyst components dissolved in methanol solvents. The proportions of the metal and alkoxide components in the catalyst formulation will vary, depending upon whether methanol is used alone as the solvent or whether a co-solvent is used. Basically, the amount of metal and alkoxide in one liter of methanol containing solvent system varies from about 0.01-2 moles of metal compound and 0.01-20 moles of alkoxide. If methanol alone is the solvent, the preferred molar ratio is 1/100 while if tetrahydrofuran is used as a co-solvent, the preferred molar ratio is 1/0.5.

Batch methanol synthesis rates as high as 300 psi/min have been achieved with the homogeneous catalysts of the present invention. The simplicity of this active catalyst lies in the fact that the product (methanol) serves as the solvent and the alkoxide component can be derived from the product making the system mechanistically simple and economically attractive. The product methanol can be removed from the reaction zone together with non-reacted CO and $H_2$ as a gas simultaneously with its formation by the chemical reaction in the liquid phase. The catalyst is extremely selective for methanol synthesis. Conversions to methanol of as high as 94% are consistently achieved. The rate at which carbon monoxide and hydrogen react can be increased by carrying out the reaction in the presence of a co-solvent. Particularly recommended are THF, 2 methyl-THF, p-dioxane, t-amyl alcohol, t-butyl alcohol, triglyme and the polyethylene glycols, known as PEG-200 and PEG-400. The above co-solvents are preferably applied in molar or almost molar proportions with respect to methanol. If desired, however, also larger or smaller quantities may be chosen.

Since the reaction between CO and $H_2$ to form methanol catalyzed by the homogeneous catalyst of the present invention occurs in a liquid reaction phase, the feed gas can be supplied to the catalyst for contacting in any reactor that is designed for liquid phase/gas system operation. Likewise, the methanol production can be carried out in a reactor system designed for batch, semi-continuous or continuous production.

It is preferred to carry out the production of methanol using the instant catalyst using a reactor that is characterized by good mixture of the gas/liquid phases. The methanol product is removed from the reactor by bubbling an excess of carbon monoxide and hydrogen, or an inert carrier gas such as nitrogen, through the reactor. By removing methanol as a gas, the technical advantages to the production process associated with the catalyst, its activity, lifetime and handling are achieved. Alternatively, methanol can be removed in the liquid phase so that dissolved catalyst is carried with product flow from the reactor. Products are flashed in a separation zone and recovered catalyst is recirculated to the reactor.

The combination of low operating temperature needed by the instant catalyst and its high catalytic activity at very short contact times makes it possible to achieve very high conversion rates of the feed gas in the methanol synthesis. Equilibrium conversion of syngas having 2 mols of hydrogen per mol of carbon monoxide at 100° C. and 150 psi has consistently been calculated to be about 94%. Furthermore, the liquid nature of the catalyst systems makes it possible to decouple gas liquid contacting for fast reaction from the removal of heat resulting from the exothermic reaction of CO and $H_2$ from the reactor. This decoupling can be done, for example, by circulating the catalyst through an external cooler or incorporating an inert low-boiling compound into the catalyst system which can be condensed externally and recycled to the reactor. The combination of the process' high thermodynamic equilibria and the ability to decouple kinetics and heat transfer overcomes reactor design limitations imposed by current catalyst technology.

In one embodiment of the present invention, the homogeneous catalyst is prepared in situ in the reactor by adding the transition metal carbonyl contributing material and the alkoxide contributing material to a solution of methanol and desired co-solvents, activators, etc. Methanol production can proceed immediately upon catalyst preparation. In an alternative approach, the homogeneous catalyst can be prepared separately in advance and loaded into the reactor when needed.

In one embodiment for methanol synthesis using the liquid phase catalyst of the present invention, feed synthesis gas enters the reactor which operates at 110° C. and 150 psi. Gas rises through the catalyst solution and forms methanol releasing heat which is removed, for example, by circulation of a coolant through coils in the reactor. Though this cooling system does not completely decouple cooling from reaction interface conditions, heat transfer to the coils is rapid and the reaction proceeds essentially isothermally at a favorable temperature because of the vigorous agitation and turbulence of the liquid induced by gas flow. As a result, conversion of 90% of the carbon monoxide can be achieved. The tail gas is, therefore, very small in volume and the cooler, separator and recycle compressor for recycling unconverted gas are very small in comparison to the requirements of similar components used with conventional heterogeneous catalysis. The small volume of gas may be insufficient to carry all the methanol overhead as vapor. In such a case, it is necessary to extract liquid from the reaction. This liquid is blended with condensate from the separator and constitutes the crude methanol which flows from the separation system. When liquid is removed from the reactor, the first distillation tower separates volatile catalyst components and returns them to the reactor. The second distillation tower produces methanol product as distillate. If this approach is taken to the production of methanol, and a co-solvent is to be used in the system, a co-solvent will be chosen that has a boiling point higher than methanol so that the methanol and co-solvent are separated in the second distillation tower and the col-solvent is returned as a liquid to the reactor.

The methanol process of the present invention is made possible by the discovery of this low temperature liquid catalyst which can convert synthesis gas almost completely to methanol in a single pass through the methanol synthesis reactor. This characteristic allows atmospheric nitrogen to be tolerated in the synthesis gas and still the volume of gas fed to the reactor can be smaller than the gas volume needed in current synthesis reactors. Table 1 below sets forth a comparison between the instant process and a conventional methanol catalysis process. Significant improvements are noted in both reaction conditions and product yields.

TABLE 1

|  | Methanol Production Catalyzed By Homogeneous Catalyst | Methanol Production By Conventional Catalysis* |
| --- | --- | --- |
| Reactor Temperature, °C. | 110 | 265 |
| Reactor pressure, psia | 150 | 750 |
| Equilibrium CO conversion, % | 94 | 61 |
| Operating CO conversion, % | 90 | 16 |
| Volume of gas recycle, mols CO/mol product | 0.11 | 5.25 |
| Reactor feed, mols CO/mol product | 1.11 | 6.25 |
| Overhead gas cooling duty, Btu/mol product | 4,100 | 71,000 |
| Separator temperature for 95% product recovery, °F. | 163 | 77 |

*Supp. E, Hydrocarbon Processing, March 1981, pp 71–75 and Hydrocarbon Processing, July 1984, pp 34C–34J The following examples will further illustrate the invention but the invention is not restricted to these examples. In the examples set forth below, the total pressure in the reactor varied from the 8765 psia at the start of each run to about 50–150 psia when the reaction was terminated; this final pressure is equivalent to the desired operating pressure of continuous reactor.

EXAMPLE 1

Sodium t-amyl alkoxide (40 mmol), prepared by reacting NaH (40 mmol) with a slight excess of t-amyl alcohol (52 mmol) in 30 mL THF, was added to the reactor along with 70 mL THF to give 100 mL total THF. The reactor was flushed with $H_2$. 10 mmol $Ni(CO)_4$ was added and the reactor was pressurized with 300 psig syngas ($2H_2$: ICO). On heating to 100° C., the gas consumption rate was 3, 8, 7 psi/min. respectively, during first, second, and third charge (300 psi each) respectively. 164 mmol methanol was produced corresponding to 86% gas consumption.

EXAMPLE 2

This example shows the effect of alkali metal on rate. The alkoxide preparation and reactor loading described in Example 1 was repeated using potassium hydride in place of sodium hydride. Thus, 40 mmol K-t-amyl alkoxide was prepared by reaction of KH (40 mmol) with 52 mmol t-amyl alcohol in 30 mL THF. The resulting solution was poured into the reactor and 70 mL additional THF was added. The reactor was sealed and purged with $H_2$ and 10 mmol $Ni(CO)_4$ was added. 300 psi syngas ($2H_2$: ICO) was added to the reactor and the reactor was heated to 100° C. The average gas consumption rate was 32, 50, 22, 7.5 psi/min for charges 1 (300 psi), 2 (300 psi), 4 (750 psi), respectively. 0.35 mol methanol was produced.

EXAMPLE 3

This example illustrates the positive effect of increasing alkoxide concentration on rate and shows that the process is truly catalytic in base and nickel. K-t-amyl alkoxide was increased to 100 mmol from 40 mmol and the procedure described in Example 2 was followed. The average rate was 54, 275, 64 psi/min for charges 1 (300 psi) and 2, 3, 4, 5 (750 psi each). 1 mol methanol corresponding to 94% gas conversion was produced. Methanol produced corresponds to at least 100 cycles in Ni and 10 cycles in base, proving the catalytic nature of the present invention.

EXAMPLE 4

Methanol (212 mmol) was produced when a mixture containing ligand, 2, 2-bipyridine (5 mmol), in addition to reagents described in Example 2 were heated at 100° C. and stirred in a reactor. The pressure drop rate was 90, 28, and 12 psi/min for charges 1, 2, and 3 (300 psi each), respectively. Methanol alone accounted for 82% gas consumption.

EXAMPLE 5

The procedure in Example 2 was followed, except that the reactor was pressurized with syngas containing $N_2$ (instead of usual $2H_2$: 1 CO mixture), methanol was produced. The gas consumption rates were 46 and 15 psi/min, respectively, for charges 1 and 2 (700 psi each containing 400 psi $N_2$ and 300 psi $2H_2$: 1 CO syngas), respectively. The $N_2$ gas simply passed through the system without affecting the catalyst. 639 mmol methanol was produced accounting for >98% total gas consumption.

EXAMPLE 6

The procedure described in Example 2 was followed, except that the gas mixture contained between 84–90% $CH_4$% instead of normal $2H_2$: 1 CO gas mixture. 153 mmol methanol was produced, accounting for >98% of the total gas consumed, showing that the methane did not affect catalyst activity.

EXAMPLE 7

The procedure described in Example 2 was followed except that the initial gas mixture contained $H_2S$. The rates were 33 and 5 psi/min for charges 1 (300 psi containing 2% $H_2S$) and 2 (300 psi containing 4% $H_2S$), respectively. 238 mmol methanol was produced, accounting for >99% total gas consumption, showing that the catalyst has high tolerance to S poison.

EXAMPLE 8

A slight improvement in conversion rate was observed when K in place of KH was used to prepare the alkoxide component. Thus, a solution containing 40 mmol K-t-amyl alkoxide (prepared from potassium (40 mmol) and t-amyl alcohol (52 mmol)), 100 mL THF, 5 mmol $Ni(CO)_4$ was heated to 100° C. under 300 psi syngas ($2H_2$:1 CO) in the reactor. 260 mmol methanol was produced. The rate was 26, 52, 25 psi/min for charges 1, 2, and 3 (300 psi each), respectively.

EXAMPLE 9

The following experiments were performed to establish the effect of the concentration of the transition metal carbonyl component of the catalyst on methanol synthesis rate. The procedure and set-up described in Example 8 was followed except that concentration of nickel tetracarbonyl was varied. Gas consumption rates are shown in Table 2 for charges 1, 2, and 3 (300 psi each).

TABLE 2

| $Ni(CO)_4$ mmol | Charge No. | Average Gas Consumption Rate psi/min | Total Methanol mmol |
|---|---|---|---|
| 1 | 1 | 4 | 230 |
|  | 2 | 19 |  |
|  | 3 | 25 |  |
| 10 | 1 | 25 | 237 |
|  | 2 | 63 |  |
|  | 3 | 32 |  |
| 20 | 1 | 26 | 245 |
|  | 2 | 80 |  |
|  | 3 | 42 |  |

At a given base concentration (40 mmol in this case) the rate increases with increasing nickel carbonyl concentration but not in linear fashion. In every case, the process is truly catalytic.

EXAMPLE 10

This example illustrates that the catalyst activity for methanol synthesis is not dependent on volume of solvent. K-t-amyl alkoxide (40 mmol) was loaded into 300 mL, Parr reactor along with 20 mL THF. After purging with $H_2$, the reactor was charged with 300 psi $2H_2$:1 CO gas mixture. The gas consumption rate was 36 psi/min. For charges 2 and 3 (300 psi each), the rates were 47 and 30 psi/min, respectively, suggesting high volumetric efficiency with the present catalyst.

EXAMPLE 11

The rate of methanol synthesis is sensitive to base/nickel ratio. Thus, when one of the experiments in Example 9 was repeated with base/nickel=100 mmol/1 mmol (100/1 ratio), the rates were 8, 40, 52 psi/min for charges 1, 2, and 3 (300 psi each), respectively.

EXAMPLE 12

The procedures described in Example 8 were repeated with potassium-t-amyl alkoxide replaced with 40 mmol K-t-butoxide (prepared from K and t-butyl alcohol). The rates were 12, 64, 30 psi/min for charges 1, 2, and 3, respectively. The rate is dependent on the nature of alcohol from which the alkoxide is derived.

EXAMPLE 13

Repeating the experiment described in Example 8 with 40 mmol potassium methoxide (KOMe) (this alkoxide is derived from MeOH, a primary alcohol as opposed to K-t-amyl alkoxide and K-t-butoxide which are derived from tertiary alcohols), a significant improvement in rate was observed (74,31, 22 psi/min for charges 1, 2, and 3, respectively). 303 mmol MeOH was produced accounting for 97% syngas consumed.

EXAMPLE 14

0.1 mol of tetramethylammonium methoxide was dissolved in 100 mL methanol diluted with 50% p-dioxane, and 5 mmol $Ni(CO)_4$ was added to provide a completely homogeneous medium. The reactor was pressurized to 800 psia with syngas ($2H_2$1CO) and heated to 120° C. The rate of methanol synthesis was 3 psi/min, comparable to that observed with $KOCH_3$ under similar conditions.

EXAMPLE 15

The procedures described in Example 8 were repeated except that the co-solvent THF was replaced with the co-solvents shown in Table 3. The rate data are presented below in Table 3.

TABLE 3

| | Rate (psi/min) | | |
|---|---|---|---|
| Solvent | Charge 1 | Charge 2 | Charge 3 |
| 2-Methyltetrahydrofuran | 22 | 17 | 4 |
| 1,2, Diethoxyethane | 34 | 12 | 4 |
| p-Dioxane | 25 | 49 | 23 |
| N-Methylmorpholine | 40 | 12 | 3 |
| t-Amyl alcohol | 2 | 1 | — |
| polyethylene glycol (PEG-400) | 52 | 32 | — |
| PEG400/Methanol (1:1 v/v) | 92 | — | — |

The homogeneous catalyst performed most efficiently when THF, p-dioxane or polyethylene glycol was used as the co-solvent.

EXAMPLE 16

200 mmol KOMe was dissolved in 100 mL of polyethylene glycol (PEG-400), and 10 mmol $Ni(CO)_4$ was added to give a completely homogeneous red solution. The reactor was pressurized with 800 psia syngas ($2H_2$:1CO) and heated to 120° C. The methanol synthesis initiated at below 50° C. and the rate was 52 and 32 psi/min for charges 1 and 2 respectively.

EXAMPLE 17

Methanol solvent was diluted with 50% PEG-400 and 400 mmol KOMe and 10 mmol $Ni(CO)_4$ was added to form deep red catalyst solution. The initial 820 psi syngas ($2H_2$:1CO) pressure in the reactor decreased to 49 psia with reaction initiating below 40° C. The methanol synthesis rate was 92 psi/min and the highest temperature achieved during the reaction was 115° C. intended temperature being 120° C. 296 mmol methanol was synthesized with methanol selectivity >98.5%. The final solution was red and completely homogeneous and 94% CO conversion was achieved in less than 5 minutes.

EXAMPLE 18

40 mmol K-t-amyl alkoxide, 100 ml THF, and 5 mmol $Ni(CO)_4$ were mixed together under argon to give a red solution. After 2 days at room temperature, the red solution was loaded into the reactor and heated to 100° C. after pressurizing to 300 psi with syngas ($2H_2$: 1 CO). The activity of the premixed catalyst was the same as that of fresh catalyst solution described in Example 8.

EXAMPLE 19

The effects of methanol build-up and base concentration on rates were studied at 110° C. and 750 psi using 5 mmol nickel tetracarbonyl, p-dioxane as the co-solvent and KOMe as the alkoxide. The results as shown in Table 4.

TABLE 4

| Solvent | | | |
|---|---|---|---|
| p-Dioxane mL | Methanol mL | Base | Rate |
| 100 | 0 | 100 | 180 |
| 90 | 10 | 100 | 102 |
| 75 | 25 | 100 | 15 |
| 50 | 50 | 100 | 3 |
| 75 | 25 | 400 | 224 |

Table 4 shows that rate decreases with increasing concentration of methanol at a given base concentration. But by simply increasing base concentration, the rate can be increased. This relationship between base/MeOH ratio is described in the following example.

EXAMPLE 20

Solutions containing 5 mmol nickel carbonyl, 100 mL methanol and potassium methoxide were heated at 110° C. under 750 psi ($2H_2$: 1 CO) syngas pressure. At higher base concentration (>400 mmol), the gas is consumed even before desired temperature is reached. The following results of this experiment show that methanol synthesis rate is dependent on the KOMe/MeOH (base/solvent) ratio.

| KOMe (mmol) | Rate (psi/min) |
|---|---|
| 400 | 11 |
| 600 | >60 |
| 800 | >>72 |

EXAMPLE 21

Catalyst solutions containing 600 mmol KOMe, 100 mL MeOH, and $Ni(CO)_4$ were heated at 110° C. under 750 psi ($2H_2$:1CO) syngas pressure. As shown in the following data, the rate increased with increasing nickel carbonyl concentration.

| $Ni(CO)_4$ | Rate |
|---|---|
| 1 | 15 |
| 5 | >60 |
| 20 | >>100 |

At higher $Ni(CO)_4$ concentrations (e.g., 20 mmol), the gas is consumed in <3 minutes with concomitant formation of methanol.

EXAMPLE 22

The effect of reaction temperature on rate of methanol synthesis was studied. When 100 mL p-dioxane containing 100 mmol KOMe and 5 mmol $Ni(CO)_4$ was pressurized to 750 psi with $1H_2$: 1 CO syngas, the rate of gas consumption was 15, 43, 63, 180 psi/1 min at 70°, 77°, 90°, 100° C., respectively. An Arrhenius plot yielded $E_{act}$=23.3 Kcal/mole for the reaction. Methanol synthesis starts as low as room temperature at higher catalyst concentrations but the system operates well between 50°-150° C.

EXAMPLE 23

The present catalyst system can tolerate several traditional poisons, which adversely affect conventional methanol catalysts, as evidenced from rate data from batch reactions. Thus, with the catalyst system with 400 mmol KOMe described in Example 20, the effect of various poisons was as follows;

(1) with 750 psi syngas containing 8% $CO_2$ (rest is $2H_2$: 1 CO), a 20% decrease in rate was observed;

(2) with 750 psi syngas containing 26% $N_2$, 7.4% $CO_2$, 2.5% $H_2S$ (rest was $2H_2$: 1 CO), the rate decreased by 50%.

EXAMPLE 24

In one embodiment of the invention, 3.0 g dry Zeolite 13X (dried under vacuum at 400° C. for 4h) was added during reactor loading along with 400 mmol KOMe in 100 mL methanol. The reactor was purged with $H_2$ and 5 mmol $Ni(CO)_4$ was added. The reactor was pressurized with 750 psi ($2H_2$: 1 CO) syngas and heated to 110° C. The rates were 10% higher compared with rates with catalyst solutions containing no Zeolite. The advantages of using a transition metal carbonyl support such as Zeolite include:

(1) virtual disappearance of methylformate, which is normally present in small amounts as a by-product; and (2) immobilization of $Ni(CO)_4$ onto the Zeolite. Gas phase infrared shown that gas phase concentration of $Ni(CO)_4$ is decreased using the Zeolite support.

EXAMPLE 25

Twenty batch experiments were conducted to determine the effects of temperature, methanol concentration, base concentration, $P_{H2}$, $P_{CO}$, and stirrer speed on reaction rate. Table 5 lists the conditions used in each run. All runs were conducted using an initial $Ni(CO)_4$ concentration of 0.05M except for Runs 1 and 2, which used an initial concentration of 0.01M. Run 21 was conducted using methyl formate as a solvent with methanol, while all other runs used either pure methanol or a methanol/p-dioxane mixture as the solvent.

The methanol, base, and $Ni(CO)_4$ liquid phase concentrations listed in Table 5 were calculated by assuming (1) no volume change on mixing of p-dioxane, methanol, and $KOCH_3$ and (2) no density change of the liquid phase from 25° C. to reaction temperature. Therefore, the methanol, $KOCH_3$, and $Ni(CO)_4$ concentrations are more accurately described as moles/liter at 25° C.

Runs 1 and 2 were the only runs conducted at an initial $Ni(CO)_4$ concentration of 0.01M because the experiments were for a catalyst concentration that would give a reasonable rate of reaction. A reasonable rate of reaction was defined as one that would take between two minutes and two hours to drop from the initial pressure of 750 psig to the final pressure of 100–150 psig. The rate of reaction in Runs 1 and 2 was relatively slow and was expected to decrease further at the lower temperatures of interest. Therefore, for all subsequent runs, a high initial $Ni(CO)_4$ concentration 0.05M was used. This concentration of $Ni(CO)_4$ gave a reasonable rate of reaction.

Runs 3 and 5 were conducted to determine if mass transfer was limiting the rate of reaction in the experiments. Runs 4, 7, 9, and 11 were conducted at 116°, 70°, 98°, and 87° C., respectively, to determine the effect of temperature on the rate of reaction. In Run 6 it was attempted to repeat Run 4, but at a lower stirrer speed, to determine if mass transfer was limiting the rate of reaction. However, Run 6 was complete before the reaction temperature reached that of Run 4.

Run 8 was the first run conducted with methanol present at the beginning of the reaction. This run was conducted at 90° C. because the rate of reaction in a more concentrated methanol solution was not known. The rate at 90° C. was slower than anticipated, hence, for all subsequent runs in which methanol was present at the start of the reaction, the reaction temperature was maintained at about 110° C.

Runs 10, 12, and 13 were conducted to determine the effect of methanol on the reaction rate. The initial methanol concentrations used in these runs were 25, 20, and 50 vol %, respectively. Runs 14, 15, and 16 were also conducted to determine the effect of methanol concentration on the reaction rate at a different catalyst base loading. These runs were conducted with initial methanol concentrations of 25, 75, and 100 vol %, respectively, and an initial $KOCH_3$ concentration of 4.0M.

Run 17, which was a repeat of Run 15 but at a higher stirrer speed, was conducted to determine if mass transfer was limiting the rate of reaction in the experiments with higher concentrations of base. Runs 18 and 19, which were a repeat of Run 16 but at higher base concentrations were conducted to determine the effect of base concentration on the reaction rate in a 100 vol % methanol solvent. Run 21, which was a repeat of Run 19 but with a 10 vol % methyl formate solvent, was conducted to determine if methyl formate affected the rate of reaction.

In addition, one experiment (Run 18) was run to demonstrate that $Ni(CO)_4$ and potassium methoxide were not consumed during the reaction and functioned as catalysts. This experiment was performed over a three-day period by repeatedly pressurizing a vessel with syngas after the reaction had lowered the pressure to below 200 psig.

TABLE 5

| | Reaction Conditions for Batch Kinetic Experiments | | | | | |
|---|---|---|---|---|---|---|
| Run Number[a] | Stirrer Speed (RPM) | Initial $KOCH_3$ Concentration (M) | Initial p-dioxane Concentration (Vol %) | Initial Methanol Concentration | | Isothermal Reaction Temperature (°C.) |
| | | | | (Vol %) | (M) | |
| 1[b] | 1200 | 0.4 | 100 | 0 | 0 | 120 |
| 2[b] | 1200 | 0.4 | 100 | 0 | 0 | 110 |
| 3 | 800 | 0.4 | 100 | 0 | 0 | 120 |
| 4 | 1200 | 1.0 | 100 | 0 | 0 | 116 |
| 5 | 1200 | 0.4 | 100 | 0 | 0 | 120 |
| 6 | 500 | 1.0 | 100 | 0 | 0 | 110 |
| 7 | 1200 | 1.0 | 100 | 0 | 0 | 70 |
| 8 | 1200 | 1.0 | 75 | 25 | 6.2 | 90 |
| 9 | 1200 | 1.0 | 100 | 0 | 0 | 98 |
| 10 | 1200 | 1.0 | 75 | 25 | 6.2 | 110 |
| 11 | 1200 | 1.0 | 100 | 0 | 0 | 87 |
| 12 | 1200 | 1.0 | 90 | 10 | 2.5 | 110 |
| 13 | 1200 | 1.0 | 50 | 50 | 12.4 | 109 |
| 14 | 1200 | 4.0 | 75 | 25 | 6.2 | 107 |
| 15 | 1200 | 4.0 | 25 | 75 | 18.5 | 110 |
| 16 | 1200 | 4.0 | 0 | 100 | 24.7 | 110 |
| 17 | 1800 | 4.0 | 25 | 75 | 18.5 | 109 |
| 18 | 1200 | 8.0 | 0 | 100 | 24.7 | 110 |
| 19 | 1200 | 6.0 | 0 | 100 | 24.7 | 109 |

TABLE 5-continued

| | | Reaction Conditions for Batch Kinetic Experiments | | | | |
|---|---|---|---|---|---|---|
| Run Number[a] | Stirrer Speed (RPM) | Initial KOCH$_3$ Concentration (M) | Initial p-dioxane Concentration (Vol %) | Initial Methanol Concentration (Vol %) | (M) | Isothermal Reaction Temperature (°C.) |
| 20[c] | 1200 | 6.0 | 0 | 90 | 22.2 | 110 |

[a]Total solvent used = 100 ml for all runs.
[b][Ni(CO)$_4$]$_0$ = 0.01 M. For all other runs, [Ni(CO$_4$)] = 0.05 M.
[c]10 vol % methyl formate was used in place of p-dioxane.

EXAMPLE 26

The following example demonstrates the synergistic effect of bimetallic systems in methanol synthesis. 1 mmol Ni(CO)$_4$, 5 mmol copper methoxide, and 0.6 mol KOCH$_3$ were dissolved in 100 mL methanol. The reactor was pressurized with syngas (2H$_2$:1CO) and heated to 120° C. Methanol was produced at a rate of about 5 psi/min.

EXAMPLE 27

5 mmol Ni(CO)$_4$ was added to a solution containing 0.4 mol KOMe dissolved in 30% methanol/70% triethyleneglycol dimethylether (triglyme) mixture and the reactor was pressurized to 750 psig syngas with H$_2$/CO of 2/1 ratio. The reactor when heated to 120° C. resulted in syngas consumption rate of 115 psi/min.

We claim:

1. A method of producing methanol in a liquid those from synthesis gas comprising hydrogen and carbon monoxide which comprises contacting said synthesis gas with a homogeneous catalyst dissolved in methanol or methanol and a co-solvent, wherein said catalyst consists of a transition metal carbonyl complex, wherein the transition metal is selected from the group consisting of Cu, Ni, Pd, Co, Ru, Mo, Fe, and mixtures thereof, and an alkoxide.

2. The method according to claim 1 wherein the transition metal is nickel and the alkoxide is an aliphatic alcoholate and methanol is used with a co-solvent selected from the group consisting of tetrahydrofuran, methyl tetrahydrofuran, p-dioxane, t-amyl alcohol, polyethylene glycol and derivatives of polyethylene glycol.

3. The method according to claim 2 wherein the alkoxide is methoxide.

4. The method according to claim 1 which comprises using low temperature, 100°-1540° C., and low pressure, 100-150 psi, condition.

5. The method according to claim 1 wherein the transition metal carbonyl complex is a complex of nickel tetracarbonyl, the alkoxide is methoxide derived from potassium methoxide, and the solvent system is methanol and a co-solvent selected from the group consisting of tetrahydrofuran, p-dioxane, polyethylene glycol and derivatives of polyethylene glycol.

6. The method according to claim 1 wherein a transition metal carbonyl activator is added to the reaction solution.

7. The method according to claim 6 wherein the activator is sodium sulfide.

8. The method according to claim 6 wherein the activator is boric acid.

9. The method according to claim 1 wherein a material is added to the reaction solution that inactivates the cation associated with the alkoxide.

10. The method according to claim 9 wherein the inactivator is a Crown ether.

11. The method according to claim 1 wherein the synthesis gas contains inert gases.

* * * * *

UNITED STATES PATENT AND TRADEMARK OFFICE
CERTIFICATE OF CORRECTION

PATENT NO.  :  4,992,480

DATED       :  Feb. 12, 1991

INVENTOR(S) :  Devinder Mahajan et al

It is certified that error appears in the above-identified patent and that said Letters Patent is hereby corrected as shown below:

Col. 13, claim 1, line 1, "those" should be --phase--.

Col. 14, claim 4, line 2, "1540°C" should be --150°C--.

Signed and Sealed this

Thirtieth Day of June, 1992

Attest:

DOUGLAS B. COMER

Attesting Officer

Acting Commissioner of Patents and Trademarks